(12) United States Patent
Getts et al.

(10) Patent No.: US 8,802,867 B2
(45) Date of Patent: *Aug. 12, 2014

(54) METHOD FOR PRODUCING A SENSE RNA MOLECULE

(75) Inventors: Robert C. Getts, Collegeville, PA (US); Jaime Boyle, Gilbertsville, PA (US)

(73) Assignee: Genisphere, LLC, Hatfield, PA (US)

( * ) Notice: Subject to any disclaimer, the term of this patent is extended or adjusted under 35 U.S.C. 154(b) by 1738 days.

This patent is subject to a terminal disclaimer.

(21) Appl. No.: 11/547,186

(22) PCT Filed: Mar. 31, 2005

(86) PCT No.: PCT/US2005/010898
§ 371 (c)(1),
(2), (4) Date: Feb. 19, 2008

(87) PCT Pub. No.: WO2005/098044
PCT Pub. Date: Oct. 20, 2005

(65) Prior Publication Data
US 2008/0160581 A1    Jul. 3, 2008

Related U.S. Application Data

(60) Provisional application No. 60/558,421, filed on Apr. 1, 2004.

(51) Int. Cl.
*C07D 207/00* (2006.01)
*C07H 21/02* (2006.01)

(52) U.S. Cl.
USPC ........................................ 548/400; 536/23.1

(58) Field of Classification Search
None
See application file for complete search history.

(56) References Cited

U.S. PATENT DOCUMENTS

| | | | | |
|---|---|---|---|---|
| 5,169,766 A | * | 12/1992 | Schuster et al. | 435/91.2 |
| 5,194,370 A | | 3/1993 | Berninger et al. | |
| 5,716,785 A | | 2/1998 | Van Gelder et al. | |
| 6,338,954 B1 | | 1/2002 | Gemen | |
| 6,794,141 B2 | * | 9/2004 | Erlander et al. | 435/6 |
| 7,494,789 B2 | * | 2/2009 | Getts et al. | 435/91.1 |
| 7,550,264 B2 | * | 6/2009 | Getts et al. | 435/6 |
| 2002/0015949 A1 | | 2/2002 | Erlander et al. | |
| 2003/0044808 A1 | | 3/2003 | Luo | |
| 2003/0104432 A1 | | 6/2003 | Xu et al. | |
| 2003/0186237 A1 | * | 10/2003 | Ginsberg et al. | 435/6 |

FOREIGN PATENT DOCUMENTS

EP    1 043 405 A2    10/2000
WO    WO-2004/101749 A2    11/2004

OTHER PUBLICATIONS

Agilent Technologies, Agilent Low RNA Input fluorescent linear Amplification Kit; Aug. 2003; Protocol of Product No. 5184-3523.*
Rajeevan t al., "Global amplification of sense RNA: a novel method to replicate and archive mRNA for gene expression analysis", Genomics, Academic Press, San Diego, US, vol. 82, No. 4, pp. 491-497, Oct. 2003.
Van Gelder et al., "Amplified RNA synthesized from limited quantities of heterogeneous cDNA", Proceedings of the National Academy of Sciences of USA, National Academy of Science, Washington, US, vol. 87, pp. 1663-1667, Mar. 1990.

* cited by examiner

*Primary Examiner* — Alexander Kim
(74) *Attorney, Agent, or Firm* — Servilla Whitney LLC

(57) ABSTRACT

Methods and kits are provided for producing sense RNA molecules. The sense RNA molecules can be used in various research and diagnostic applications, such as gene expression studies involving nucleic acid microarrays.

32 Claims, 3 Drawing Sheets

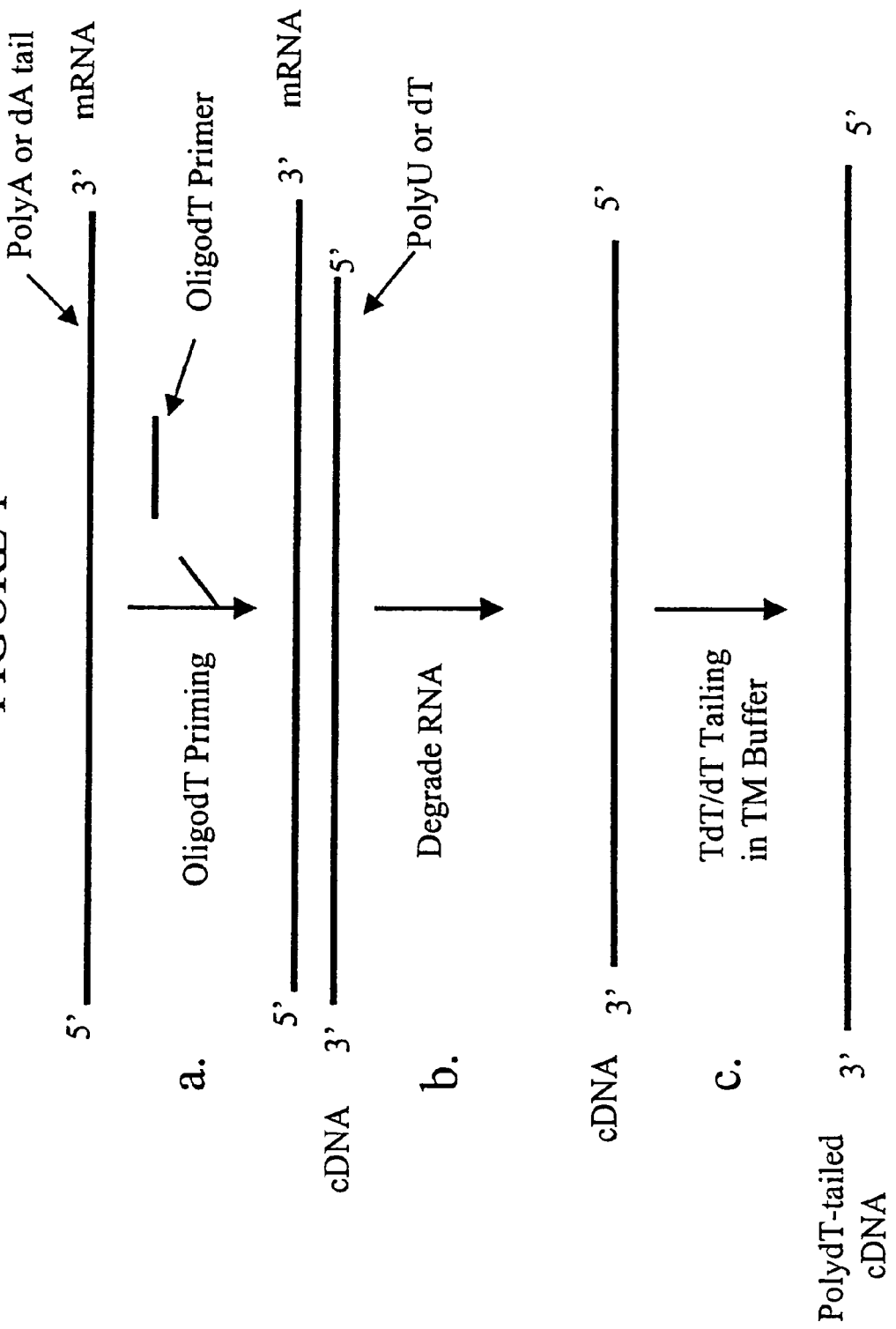

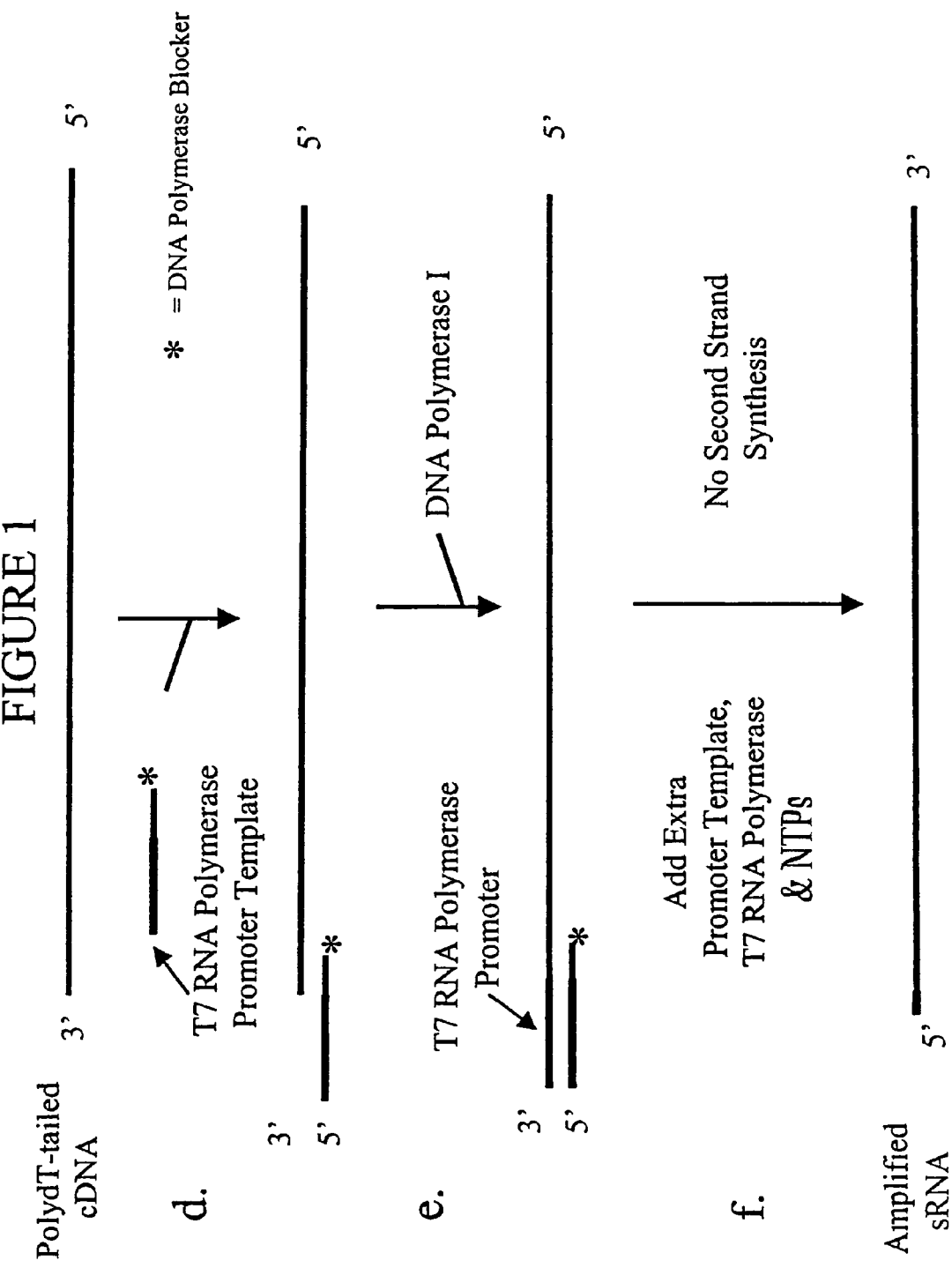

A: 123 bp Ladder
B: MessageAmp™ 1.4 µg aRNA
C: MessageAmp™ 3.5 µg aRNA
D: MessageAmp™ 7.0 µg aRNA
E: SenseAmp 1.5 µg sRNA
F: SenseAmp 2.5 µg sRNA
G: SenseAmp 6.0 µg sRNA

A B C D E F G

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: T7 polymerase promoter sense sequence

<400> SEQUENCE: 1
taatacgact cactataggg                                              20

<210> SEQ ID NO 2
<211> LENGTH: 19
<212> TYPE: DNA
<213> ORGANISM: Artificial Sequence
<220> FEATURE:
<223> OTHER INFORMATION: T3 polymerase promoter sense sequence

<400> SEQUENCE: 2
aattaaccct cactaaagg                                               19

<210> SEQ ID NO 3
<211> LENGTH: 22
<212> TYPE: DNA
<213> ORGANISM: Artificial Sequence
<220> FEATURE:
<223> OTHER INFORMATION: SP6 polymerase promoter sense sequence

<400> SEQUENCE: 3
aatttaaggt gacactatag aa                                           22

<210> SEQ ID NO 4
<211> LENGTH: 24
<212> TYPE: DNA
<213> ORGANISM: Artificial Sequence
<220> FEATURE:
<223> OTHER INFORMATION: oligo dT primer

<400> SEQUENCE: 4
```

```
tttttttttt tttttttttt tttt                                              24

<210> SEQ ID NO 5
<211> LENGTH: 37
<212> TYPE: DNA
<213> ORGANISM: Artificial Sequence
<220> FEATURE:
<223> OTHER INFORMATION: T7 RNA polymerase promoter template with 3'
      amino modifier
<220> FEATURE:
<221> NAME/KEY: modified_base
<222> LOCATION: (37)..(37)
<223> OTHER INFORMATION: amino modifier

<400> SEQUENCE: 5
taatacgact cactataggg aaaaaaaaaa aaaaaaa                                 37
```

METHOD FOR PRODUCING A SENSE RNA MOLECULE

CROSS REFERENCE TO RELATED APPLICATIONS

The present application is a national phase entry under 35 U.S.C. §371 of International Application No. PCT/US2005/010898, filed Mar. 31, 2005, published in English, which claims benefit of U.S. Provisional Patent Application No. 60/558,421, filed Apr. 1, 2004. The disclosures of all of said applications are incorporated by reference herein.

TECHNICAL FIELD

The invention relates to the field of amplification of nucleic acids.

CROSS REFERENCE TO SEQUENCE LISTING

The Sequence Listing created on Mar. 14, 2011, and identified as "DSC0034-00US_ST25.txt" (1,415 bytes) is hereby incorporated by reference.

BACKGROUND ART

Microarray technology has become a powerful tool for generating and analyzing gene expression profiles. Microarray expression analysis, however, generally demands large amounts of RNA that are often not available (see Wang, et al., BioTechniques 34:394-400 (2003)). Several RNA amplification techniques have been developed to overcome this problem. These techniques, however, generally suffer from a phenomenon known as amplification bias (see, e.g., U.S. Pat. No. 6,582,906). In these cases, the amplified population of RNA molecules does not proportionally represent the population of RNA molecules existing in the original sample.

For example, in the method disclosed by Eberwine and colleagues (see, e.g., U.S. Pat. Nos. 5,545,522; 5,716,785; 5,891,636; 5,958,688; and 6,291,170), a compound oligonucleotide is utilized for the amplification, wherein the compound oligonucleotide is provided with both a T7 promoter and a primer. A cDNA copy is created of an initial mRNA transcript using the compound oliognucleotide, with subsequent second strand synthesis to create a cDNA that is double stranded. RNA amplification is conducted via the promoter portion of the compound oligonucleotide, with transcription proceeding off of the cDNA's second strand. Since the second strand is used for transcription, the Eberwine method produces amplified RNA that is antisense to the initial mRNA sequence.

The Eberwine method, however, introduces a 3' bias during each of its steps due to the incomplete processivities (i.e., the inability of an enzyme to remain attached to a nucleic acid molecule) of the enzymes utilized and the positioning of the RNA polymerase promoter (see, e.g., U.S. Pat. No. 6,582,906 and U.S. Patent Publication US2003/0104432). For example, the compound oligonucleotide used to produce first strand cDNA places the promoter at the 5' end of the cDNA, which corresponds to the 3' end of the message. This coupled with the inability of RNA polymerase to complete transcription of some templates (due perhaps to long polyA tail regions or interference from secondary and tertiary structures in the template) can result in a 3' bias in the amplified antisense RNA population. In addition, if second strand cDNA synthesis by DNA polymerase is incomplete, these cDNAs will lack functional promoters, resulting in a reduced representation of the original RNA molecule (or possibly a complete absence) in the amplified population.

SUMMARY OF THE INVENTION

Applicants have invented methods for the production of sense RNA (sRNA) molecules from various nucleic acid templates, wherein a single stranded RNA polymerase promoter that is not extendable with DNA polymerase is used for in vitro transcription of sRNA molecules. Applicants have discovered that the use of an unextendable promoter template is more efficient than the use of a promoter primer that can serve as an initiation point for DNA polymerase-mediated second strand cDNA synthesis.

One aspect of the present invention is directed to a method for producing a sRNA molecule, comprising: providing a single stranded cDNA molecule having 5' and 3' ends; attaching an oligodeoxynucleotide tail onto the 3' end of the single stranded cDNA molecule; annealing a single stranded RNA polymerase promoter template to the oligodeoxynucleotide tail, wherein the single stranded RNA polymerase promoter template is not extendable with DNA polymerase; extending the oligodeoxynucleotide tail such that the single stranded RNA polymerase promoter template is converted to a double stranded RNA polymerase promoter; and initiating RNA transcription using an RNA polymerase which recognizes the double stranded RNA polymerase promoter, thereby producing a sRNA molecule.

Another aspect of the present invention is directed to a method for producing a sRNA molecule, comprising: providing a RNA, e.g., mRNA, transcript having 5' and 3' ends; synthesizing a single stranded cDNA molecule having 5' and 3' ends from the RNA, e.g., mRNA, transcript; attaching an oligodeoxynucleotide tail onto the 3' end of the single stranded cDNA molecule; annealing a single stranded RNA polymerase promoter template to the oligodeoxynucleotide tail, wherein the single stranded RNA polymerase promoter template is not extendable with DNA polymerase; extending the oligodeoxynucleotide tail such that the single stranded RNA polymerase promoter template is converted to a double stranded RNA polymerase promoter; and initiating RNA transcription using an RNA polymerase which recognizes the double stranded RNA polymerase promoter, thereby producing a sRNA molecule.

Applicants have also invented kits for the production of sense RNA molecules from various nucleic acid templates, wherein a single stranded RNA polymerase promoter template that is not extendable with DNA polymerase is used for in vitro transcription of sRNA molecules.

Thus, a further aspect of the present invention is directed to a kit for producing at least one sRNA molecule comprising: a single stranded RNA polymerase promoter template that is not extendable with DNA polymerase, and instructional materials for producing sRNA molecules using the template. In some embodiments, the kit further comprises at least one enzyme for attaching an oligodeoxynucleotide tail onto the 3' end of a single stranded cDNA molecule having 5' and 3' ends, and at least one enzyme for converting the RNA polymerase promoter template to a double stranded RNA polymerase promoter.

BRIEF DESCRIPTION OF THE DRAWINGS

FIGS. 1a-f together are a flowchart depicting an embodiment of the methods of the present invention.

BEST MODE FOR CARRYING OUT THE INVENTION

Figure 2:
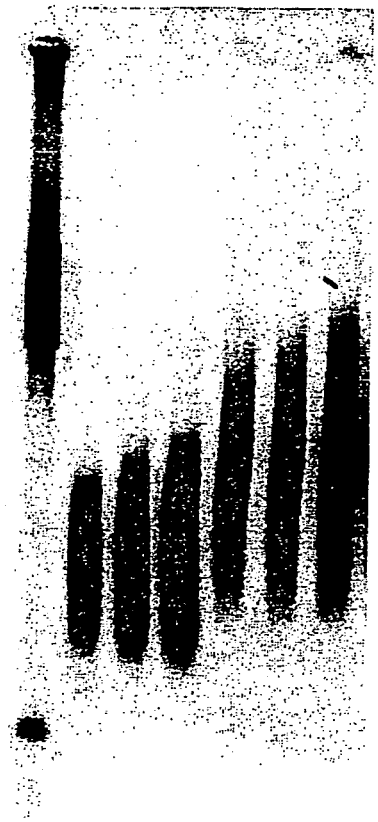
FIG. 2 is a photograph that depicts various amounts of sRNA produced by the methods of the current invention visualized on a 1% agarose denaturing gel stained with ethidium bromide.

The present invention relates to methods and kits for the generation of sRNA molecules. The terms "sRNA molecule", "RNA molecule", "mRNA molecule" and "cDNA molecule" are each intended to cover a single molecule, a plurality of molecules of a single species, and a plurality of molecules of different species. The methods comprise attaching an oligodeoxynucleotide tail onto the 3' end of at least one single stranded cDNA molecule; annealing a single stranded RNA polymerase promoter template to the oligodeoxynucleotide tail, wherein the single stranded RNA polymerase promoter template is not extendable with DNA polymerase; and extending the oligodeoxynucleotide tail such that the single stranded RNA polymerase promoter template is converted to a double stranded RNA polymerase promoter. The resulting promoter-containing single stranded cDNA is then used in an in vitro transcription reaction with RNA polymerase to produce one or more sRNA molecules. Such sRNA molecules represent amplified copies of the original RNA (e.g., mRNA) transcript from which the single stranded cDNA was obtained.

The methods of the present invention are distinct over currently available technologies that incorporate a promoter sequence onto the 5' end of first strand cDNA molecules. In those technologies, RNA-transcription proceeds in the same direction as first strand cDNA synthesis relative to the original mRNA transcript, resulting in the production of antisense RNA molecules containing a bias in favor of nucleotides proximal to the 3' polyA tail of the original mRNA transcripts. By incorporating the promoter sequence onto the 3' end of the cDNA molecules, the methods of the present invention allow genetic information at both ends of the original RNA, e.g., mRNA, transcripts to be copied and amplified. The resulting sRNA molecules are more representative of the entire length of each original RNA, e.g., mRNA, transcript and better reflect the relative abundance of each RNA, e.g., mRNA, transcript in a mixture of mRNA transcripts than those obtained by prior art methods. The methods of the current invention can also be coupled with random priming without the introduction of any added priming bias. The sRNA molecules may contain polyA tails for more efficient use in downstream assays. Additionally, the methods of the present invention are more efficient than currently available technologies due to the incorporation of an RNA polymerase promoter template blocked at its 3' end, which prevents problematic second strand cDNA synthesis during DNA polymerase-mediated conversion of the template to a double stranded RNA polymerase promoter (see, e.g., WO 02/065093).

The methods of the present invention utilize routine techniques in the field of molecular biology. Basic texts disclosing general molecular biology methods include Sambrook, et al., *Molecular Cloning, A Laboratory Manual* (3d ed. 2001) and Ausubel et al., *Current Protocols in Molecular Biology* ((1994).

Numerous methods and commercial kits for the synthesis of first strand cDNA molecules are well known in the art Examples include the Superscript™ Double Strand cDNA Synthesis kit (Invitrogen, Carlsbad, Calif.), the Array 50™, Array 350™ and Array 900™ Detection kits (Genisphere, Hatfield, Pa.), and the CyScribe™ Post-Labelling kit (Amersham, Piscataway, N.J.). In general, high quality mRNA molecules (i.e., original mRNA transcripts) from a source of interest are used as templates in a reverse transcription reaction. The RNA may be obtained from any tissue or cell source, include ng virion, prokaryotic, and eukaryotic sources found in any biological or environmental sample. Preferably, the source is eukaryotic tissue, more preferably mammalian tissue, and most preferably human tissue. In other embodiments, the template RNA may be in the form of micro RNA ("miRNA"). Micro-RNAs are a very large group of small RNAs produced naturally in organisms, at least some of which regulate the expression of target genes. MiRNAs can be prepared from RNA using standard techniques, e.g., the Micro RNA isolation kit (Stratagene, La Jolla, Calif.); Quick-Prep Micro RNA Purification Kit (Amersham Pharmacia Biotech Inc., Piscataway, N.J.).

Any reverse transcriptase can be used in the reverse transcription reaction, including thermostable and RNase H⁻ reverse transcriptases. Preferably, an RNase H⁻ reverse transcriptase is used.

Primers for first strand cDNA synthesis can be obtained commercially or synthesized and purified using techniques well known in the art. Primers for first strand cDNA synthesis include single strand oligodeoxynucleotides comprising an oligodT tail at their 3' ends. The tails generally range from about 10 to about 30 nucleotides in length, preferably from about 17 to about 24 nucleotides in length, and anneal to any original RNA, e.g., mRNA, transcript containing a 3' polyA tail (see FIG. 1a). Alternatively, the reverse transcription reaction can be initiated using a random primer. The primer generally ranges from about 4 to about 20 nucleotides in length, preferably from about 6 to about 9 nucleotides in length, and anneals to various positions along the length of each original RNA, e.g., mRNA, transcript. One of ordinary skill in the art will recognize that the use of a random primer can ultimately result in the production of sRNA molecules that are better representative of the entire length of each original RNA, e.g., mRNA, transcript than those produced using an oligodT primer. Additionally, the use of a random primer to generate cDNA in the initial steps of the disclosed methods means that RNA that would normally be exempt from amplification, such as degraded RNA or RNA derived from bacteria, can be used to produce amplified sRNA molecules. The random primer can be modified to include an oligodT region at its 5' end, ranging from about 10 to about 30 nucleotides in length, preferably from about 17 to about 24 nucleotides in length, such that amplified sRNA molecules produced during subsequent in vitro transcription will contain polyA tails.

Following first strand cDNA synthesis, the RNA is generally degraded prior to purification of the first strand cDNA molecules (see FIG. 1b). Any method that degrades RNA can be used, such as treatment with NaOH. Alternatively, the RNA can be left intact, with the first strand cDNA molecules purified from RNA/cDNA duplexes. Numerous methods and kits exist for the purification of DNA molecules. Examples include the MinElute™ PCR Purification kit (Qiagen, Valencia, Calif.), the SpinPrep™ PCR Clean-up kit (Novagen, Madison, Wis.), and other purification systems based on similar DNA fractionation principles.

Following first strand cDNA purification, a single stranded oligodeoxynucleotide tail is attached to the 3' end of the cDNA molecules (see FIG. 1c). The oligodeoxynucleotide tail can be incorporated by any means that attaches deoxynucleotides to single stranded DNA. Preferably, the oligodeoxynucleotide tail is attached to the single stranded cDNA using terminal deoxynucleotidyl transferase, or other suitable enzyme, in the presence of appropriate deoxynucleotides. Preferably, the oligodeoxynucleotide tail is a homopolymeric tail (i.e., polydA, polydG, polydC, or polydT). Preferably, the oligodeoxynucleotide tail is a polydT tail, generally ranging from about 3 to greater than 500 nucleotides in length, preferably from about 20 to about 100 nucleotides in length.

Following attachment of the single stranded oligonucleotide tail to the 3' end of the single stranded cDNA molecules, a single stranded RNA polymerase promoter template is attached to the 3' oligodeoxynucleotide tail (see FIG. 1d). This is accomplished through complementary base pairing between the 3' oligodeoxynucleotide tail and a complementary series of deoxynucleotides present at the 3' end of the single stranded RNA polymerase promoter template. For example, if oligonucleotide tail is a polydT tail, the promoter template will contain a sequence of adenosine bases at its 3' end, generally ranging from about 3 to greater than 50 nucleotides in length, preferably from about 10 to about 30 nucleotides in length. The particular nucleotide sequence of the 3' promoter template sequence does not have to be perfectly complementary to the particular nucleotide sequence of the 3' oligodeoxynucleotide tail, nor does the length of the 3' promoter template sequence need to be identical to the length of the 3' oligodeoxynucleotide tail, for the sequences to be considered complementary to each other. Those of skill in the art will recognize that all that is required is that there be sufficient complementarity between the two sequences so that the RNA polymerase promoter template will anneal to the oligodeoxynucleotide tail at the 3' end of the cDNA molecules.

The single stranded RNA polymerase promoter template also contains at its 5' end a promoter sequence specifically recognized by an RNA polymerase. Any RNA polymerase can be used, so long as a specific promoter sequence is known that is recognized by the polymerase. Preferably, the promoter sequence used is recognized by a bacteriophage RNA polymerase, such as T7, T3, or SP6 RNA polymerase. An exemplary T7 polymerase promoter sense sequence is TAATACGACTCACTATAGGG (SEQ ID NO:1). An exemplary T3 polymerase promoter sense sequence is AATTAACCCTCACTAAAGG (SEQ ID NO:2). An exemplary SP6 polymerase promoter sense sequence is AATTTAAGGTGACACTATAGAA (SEQ ID NO:3).

The single stranded RNA polymerase promoter template is also blocked at its 3' end such that it is not extendable with DNA polymerase. As such, the addition of a DNA polymerase (such as Klenow DNA polymerase) converts the single stranded promoter template into a double stranded RNA polymerase promoter, but does not catalyze the synthesis of second strand cDNA (see FIG. 1e). Applicants have found that use of a promoter template that is incapable of being extended with DNA polymerase more accurately maintains the relative abundance of mRNA transcripts found in an unamplified RNA sample than the use of a promoter primer that can serve as an initiation point for DNA polymerase-mediated second strand cDNA synthesis. The promoter template can be blocked by any means that renders it incapable of being extended with DNA polymerase, such as by including terminal blocking groups, compounds, or moieties either attached during or after synthesis. Preferably, the promoter template is blocked with a 3' amino modifier, a 3' deoxyterminator, a 3' dideoxyterminator, or similar molecule. A suitable blocker should not be restricted to any of those described herein and can include any moiety that would prevent DNA polymerase from extending the 3' terminus of the RNA polymerase promoter template.

Although the methods of present invention are preferably performed in the absence of second strand cDNA synthesis, one of skill in the art will recognize that second strand cDNA can be optionally synthesized during conversion of the single stranded promoter template into a double stranded RNA polymerase promoter by using a random primer. The random primer will anneal at various positions along the first strand cDNA and unlike the promoter template, can be extended by DNA polymerase during promoter synthesis. The various second strand cDNA fragments can be optionally ligated together to form a single second strand cDNA molecule. Such second strand cDNA molecules may stabilize (e.g., remove secondary and tertiary structure) the first strand cDNA during in vitro transcription, resulting in a higher yield of sRNA molecules.

Following conversion of the single stranded promoter template into a double stranded RNA polymerase promoter, in vitro transcription is initiated by the addition of the appropriate RNA polymerase and ribonucleotides (see FIG. 1f). Such transcription can result in the production of large amounts of amplified sRNA. Methods and kits for performing in vitro transcription are well known in the art and include the MEGAscript™ Transcription kit (Ambion, Austin, Tex.) and the AmpliScribe™ High Yield Transcription kits (Epicentre Technologies, Madison, Wis.).

The resulting sRNA molecules can be subjected to additional rounds of amplification using the same methodology as just described. For example, sRNA molecules produced from oligodT-mediated first strand cDNA (i.e., first round sRNA molecules) will have regenerated polyA tails at their 3' ends, which can serve as priming sites for a second round of oligodT-mediated first strand cDNA synthesis. Alternatively, a random primer can be used to reverse transcribe first strand cDNA from the first round sRNA molecules. Combinations and mixtures of oligodT and random primers can also be used for second round cDNA synthesis. A promoter template is then added to the second round cDNA molecules as described above, followed by a second round of in vitro transcription with the appropriate RNA polymerase. Performing additional rounds of amplification allows smaller amounts of mRNA to be used in the initial round of amplification.

PolyA tails can be added to the 3' ends of amplified sRNA molecules that lack polyA tails (such as those produced from conventional random primer-mediated first strand cDNA) using commercially available polyA tailing kits. An example of such a kit is the Poly(A) Tailing kit (Ambion). Alternatively, polyA polymerase (available from Amersham, Invitrogen, and Ambion) combined with ATP and the amplified sRNA molecules in the appropriate buffer can be used to synthesize a polyA tail on the 3' ends of the sRNA molecules. Adding polyA tails increases the number and type of downstream assays in which the amplified sRNA molecules can be used, as well as allowing the use of more inexpensive RNA labeling alternatives in those assays.

The sRNA molecules produced by the methods of the present invention can be used directly for any purpose mRNA is typically used for, including gene expression studies, genetic cloning, and subtractive hybridization. For example, the sRNA molecules may be first reverse transcribed into cDNA molecules using random primers, oligodT primers, or combinations thereof. The reverse transcription reaction can be performed in the presence of detectably labeled nucleotides, such as fluorescently labeled nucleotides. Such nucleotides include nucleotides labeled with Cy3 and Cy5. Alternatively, the cDNA molecules are labeled post-synthesis. Preferably, the cDNA molecules are labeled post-synthesis using 3DNA™ technology (Genisphere), via a nucleic acid dendrimer. These dendrimers are further described in Nilsen, et al., J. Theor. Biol., 187:273-284 (1997); in Stears, et al., Physiol. Genomics 3:93-99 (2000); and in U.S. Pat. Nos. 5,175,270; 5,484,904; 5,487,973; 6,072,043; 6,110,687; and 6,117,631.

The labeled single stranded cDNA molecules produced from the sRNA molecules of the present invention are useful as probes for gene expression studies. The cDNA molecules can be annealed to a nucleic acid microarray containing complementary polynucleotides. Preferably, the microarray is a GeneChip® microarray (Affymetrix, Santa Clara, Calif.). Because the sRNA molecules produced by the present methods are more representative of the entire length of each original RNA, e.g., mRNA, transcript and better reflect the relative abundance of each original RNA, e.g., mRNA, transcript, the results obtained for gene expression studies may be more meaningful (e.g., accurate) than those obtained using prior nucleic acid amplification techniques.

The present invention further provides kits or packages containing reagents for the practice of the inventive methods. Such kits can be used in various research and diagnostic applications. For example, methods and kits of the present invention can be used to facilitate a comparative analysis of expression of one or more genes in different cells or tissues, different subpopulations of the same cells or tissues, different physiological states of the same cells or tissue, different developmental stages of the same cells or tissue, or different cell populations of the same tissue. Such analyses can reveal statistically significant differences in the levels of gene expression, which, depending on the cells or tissues analyzed, can then be used to facilitate diagnosis of various disease states.

A wide variety of kits may be prepared according to present invention. For example, a kit may include a single stranded RNA polymerase promoter template that is not extendable with DNA polymerase (e.g., the template having a 3' blocker or blocking moiety attached thereto) and instructional materials for generating sRNA molecules using the template. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may also include one or more of the following components or reagents: a reverse transcriptase; an RNase inhibitor; an enzyme for attaching an oligodeoxynucleotide tail onto single stranded cDNA molecules (e.g., terminal deoxynucleotidyl transferase); an enzyme for converting the RNA polymerase promoter template to a double stranded RNA polymerase promoter (e.g., Klenow enzyme); and an RNA polymerase that recognizes the promoter (e.g., T7 RNA polymerase). The kits may further include buffers, primers (e.g., oligodT primers, random primers), nucleotides, labeled nucleotides, RNase-free water, containers, vials, reaction tubes, and the like compatible with the generation of sRNA molecules according to the methods of the present invention. The components and reagents may be provided individually or in combination in containers with suitable storage media.

Specific embodiments according to the methods of the present invention will now be described in the following examples. The examples are illustrative only, and are not intended to limit the remainder of the disclosure in any way.

EXAMPLES

Example 1

First Strand cDNA Synthesis

Briefly, 1-10 µl total rat brain RNA (up to 1 µg), purified using the RNAqueous® kit (Ambion) was mixed with 2 µl oligodT$_{24}$ primer (50 ng/µl) (5'-TTT TTT TTT TTT TTT TTT TTT TTT-3'; SEQ ID NO:4) and brought up to 11 µl with RNase-free water. The RNA/primer mixture was heated at 80° C. for 10 minutes and immediately cooled on ice for 1-2 min. The mixture was then mixed with 9 µl of a master mixture solution to bring the final volume to 20 µl containing 50 mM Tris-HCl (pH 8.3), 75 mM KCl, 3 mM MgCl$_2$, 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. The reaction was stopped by addition of 3.5 µl 0.5 M NaOH/50 mM EDTA and heating at 65° C. for 15 min. Following brief centrifugation, the reaction was neutralized with 5 µl 1 M Tris-HCl, pH 7.5 and adjusted to 50 µl with 1×TE, pH 8.0. The reaction was purified using the MinElute™ PCR Purification Kit (Qiagen) according to the manufacturer's protocol. The first strand cDNA molecules were eluted with 10 µl EB buffer provided by the manufacturer.

Tailing of First Strand cDNA

The first strand cDNA molecules were heated at 80° C. for 10 minutes and immediately cooled on ice for 1-2 min. The cDNA molecules in 10 µl were then mixed with 15 µl of a master mixture solution to bring the final volume to 25 µl containing 6.5 µl RNase-free water, 1× tailing buffer (10 mM Tris-HCl, pH 7.0, 10 mM MgCl$_2$), 1.5 mM dTTP, and 30 U terminal deoxynucleotidyl transferase (Invitrogen). The mixture was briefly centrifuged and incubated at 37° C. for 30 min. The reaction was stopped by heating at 80° C. for 15 min and cooling at room temperature for 1-2 min.

T7 Promoter Synthesis

Two µl of T7 RNA polymerase promoter template (250 ng/µl) containing a 3' amino modifier (5'-TAA TAC GAC TCA CTA TAG GGA AAA AAA AAA AAA AAA AX-3'; SEQ ID NO:5) was added to the oligodT-tailed cDNA molecules and the mixture incubated at 37° C. for 10 min to anneal the strands. The tailed cDNA/promoter template mixture in 27 µl was then mixed with 23 µl of a master mixture solution to bring the final volume to 50 µl containing 14 µl RNase-free water, 1× polymerase buffer (10 mM Tris-HCl, pH 7.0, 10 mM MgCl$_2$), 0.4 mM each nNTP, and 20 U Large DNA polymerase I (Klenow enzyme) (Roche Applied Science, Indianapolis, Ind.) The mixture was briefly centrifuged and incubated at room temperature for 30 min. The reaction was adjusted to 100 µl with 1×TE, pH 8.0. The reaction was purified using the MinElute™ PCR Purification Kit according to the manufacturer's protocol. The T7 promoter-cDNA molecules were eluted with 10 µl EB buffer provided by the manufacturer.

In Vitro Transcription

One µl of T7 RNA polymerase promoter template was added to the T7 promoter-cDNA molecules and the volume adjusted to 17 µl with RNase-water. The mixture was heated at 37° C. for 10-15 min to re-anneal the T7 promoter DNA strands and then mixed with 13 µl of a master mixture solution to bring the final volume to 30 µl containing 1× reaction buffer, 5 mM each rNTP, and 2 µl T7 RNA polymerase (ME-GAscript™ Transcription kit, Ambion). The mixture was briefly centrifuged and incubated in a 37° C. heat block for 15 min, followed by incubation in an air hybridization oven at 37° C. for 6-14 hrs. The amplified sRNA molecules were purified using. Rneasy® Kit according to the manufacturer's protocol. The sRNA molecules were eluted in 50 µl RNase-free water, re-eluted with the same eluate, and quantified by UV-spectrophotometry at a wavelength ratio of 260/280.

Example 2

The methodology of Example 1 was followed, but first strand cDNA synthesis was performed using a random primer instead of oligodT$_{24}$ primer. Briefly, 1-10 µl total RNA (up to 1 µg) was mixed with 2 µl random 9 mer primer (250 ng/µl) (5'-NNN NNN NNN 3') and brought up to 11 µl with RNase-free water. The RNA/primer mixture was heated at 80° C. for 10 minutes and immediately cooled on ice for 1-2 min. The mixture was then mixed with 9 µl of a master mixture solution to bring the final volume to 20 µl containing 50 mM Tris-HCl (pH 8.3), 75 mM KCl, 3 mM MgCl$_2$, 10 mM dithiothreitol, 0.5 mM each dNTP, 10 U Superase-In™, and 200 U Superscript™ II reverse transcriptase. The mixture was briefly centrifuged and incubated at 42° C. for 2 hrs. The reaction was stopped by addition of 3.5 µl 0.5M NaOH/50 mM EDTA and heating at 65° C. for 15 min. Following brief centrifugation, the reaction was neutralized with 5 µl 1 M Tris-HCl, pH 7.5 and adjusted to 50 µl with 1×TE, pH 8.0. The reaction was purified using the MinElute™ PCR Purification Kit according to the manufacturer's protocol. The first strand cDNA molecules were eluted with 10 µl EB buffer provided by the manufacturer and further processed as described in Example 1.

Example 3

Either of the methodologies of Examples 1 and 2 was followed, but RNA after first strand cDNA synthesis was left intact (i.e., no base hydrolysis) prior to application to the MinElute™ purification column. The first strand cDNA molecules were eluted with 10 µl EB buffer provided by the manufacturer and further processed as described in Example 1.

Example 4

PolyA tails were added to the amplified sRNA molecules produced by the random primer methodologies of Examples 2 and 3 using the Poly(A) Tailing kit (Ambion). The PolyA-tailed sRNA was converted to labeled cDNA using the Array 350™ Detection kit (Genisphere) and hybridized to microarrays by standard techniques as published in the product manual for the detection kit.

Example 5

Various amounts of sRNA produced by the above-described methods were visualized on a 1% agarose denaturing gel stained with ethidium bromide. As can be seen in FIG. 2, the methods of the current invention (identified as SenseAmp, lanes E-G) produce larger amplified RNA molecules as compared to a commercially available, Eberwine-based method (identified as MessageAmp™, Ambion, lanes B-D). Yields of up to ~1000-fold amplification over starting RNA samples were achieved using the present methods. Experimental data generated from a comparison of the amplified antisense RNA (aRNA) produced using MessageAmp™ and the amplified sRNA produced using the present methods indicated that the present methods were more accurate than the Eberwine-based method in maintaining the relative abundance of mRNA transcripts found in the original unamplified RNA sample. The Pearson Log-correlation coefficients were 0.93 and 0.86, respectively. A perfect correlation between the unamplified and amplified samples would be reflected by a Pearson Log correlation of 1.00.

Example 6

Either of the oligodT methodologies of Examples 1 and 3 was followed, but the purified sRNA molecules were subjected to a second round of RNA amplification. Briefly, the in vitro transcription reaction containing the first round amplified sRNA molecules were eluted from the Rneasy® column in 30 µl RNase-free water and re-eluted with the same eluate. The eluate was mixed with 1 µl oligodT$_{24}$ primer (50 ng/µl) (SEQ ID NO:4) and 2 µl random 9 mer primer (25 ng/µl) (SEQ ID NO:6) and brought up to 37 µl with RNase-free water. The RNA/primer mixture was heated at 80° C. for 10 minutes and immediately cooled on ice for 1-2 min. The mixture was then mixed with 23 µl of a master mixture solution to bring the final volume to 60 µl containing 50 mM Tris-HCl (pH 8.3), 75 mM KCl, 3 mM MgCl$_2$, 10 mM dithiothreitol (DTT), 0.33 mM each dNTP, 10 U Superase-In™ and 200 U Superscript™ II reverse transcriptase. The mixture was briefly centrifuged and incubated at 42° C. for 2 hrs. The reaction was adjusted to 100 µl with 1×TE, pH 8.0. The reaction was purified using the MinElute™ PCR Purification Kit according to the manufacturer's protocol. The first strand cDNA molecules were eluted with 10 µl EB buffer provided by the manufacturer.

The first strand cDNA molecules were heated at 80° C. for 10 minutes and immediately cooled on ice for 1-2 min. The cDNA molecules in 10 µl were then mixed with 15 µl of a master mixture solution to bring the final volume to 25 µl containing 6.5 µl RNase-free water, 1× tailing buffer (10 mM Tris-HCl, pH 7.0, 10 mM MgCl$_2$), 1.5 mM dTTP, and 30 U terminal deoxynucleotidyl transferase. The mixture was briefly centrifuged and incubated at 37° C. for 30 min. The reaction was stopped by heating at 80° C. for 15 min and cooling at room temperature for 1-2 min.

Two µl of T7 RNA polymerase promoter template (250 ng/µl) containing a 3' amino modifier (SEQ ID NO:5) was added to the oligodT-tailed cDNA molecules and the mixture incubated at 37° C. for 10 min to anneal the strands. The tailed cDNA/promoter template mixture in 27 µl was then mixed with 23 µl of a master mixture solution to bring the final volume to 50 µl containing 14 µl RNase-free water, 1× polymerase buffer (10 mM Tris-HCl, pH 7.0, 10 mM MgCl$_2$), 0.4 mM each nNTP, and 20 U Large DNA polymerase I (Klenow enzyme). The mixture was briefly centrifuged and incubated at room temperature for 30 min. The reaction was adjusted to 100 l with 1×TE, pH 8.0. The reaction was purified using the MinElute™ PCR Purification Kit according to the manufacturer's protocol. The T7 promoter-cDNA molecules were eluted with 10 µl EB buffer provided by the manufacturer.

One µl of T7 RNA polymerase promoter template was added to the T7 promoter-cDNA molecules and the volume adjusted to 16 µl with RNase-water. The mixture was heated at 37° C. for 10-15 min to re-anneal the T7 promoter DNA strands and then mixed with 24 µl of a master mixture solution to bring the final volume to 40 µl containing 1× reaction buffer, 7.5 mM each rNTP, and 4 µl T7 RNA polymerase (MEGAscript™ Transcription kit). The mixture was briefly centrifuged and incubated in a 37° C. heat block for 15 min, followed by incubation in an air hybridization oven at 37° C. for 6-14 hrs. The amplified second round sRNA molecules were purified using Rneasy® Kit according to the manufacturer's protocol. The second round sRNA molecules were eluted in 50 µl RNase-free water, re-eluted with the same eluate, quantified by UV-spectrophotometry at a wavelength ratio of 260/280, and visualized on a 1% agarose denaturing gel stained with ethidium bromide.

Example 7

A kit for the production of sRNA molecules was assembled with the following components:

OligodT$_{24}$ Primer (50 ng/µl);
Random 9 mer Primer (250 ng/µl);
dNTP Mix (10 mM each);
Superase-In™ (Ambion);
dTTP Tailing Mix (10 mM);
10× Reaction Buffer (100 mM Tris-HCl, pH 7.0, 100 nM MgCl$_2$);
Terminal Deoxynucleotidyl Transferase (15-30 U/µl);
T7 RNA Polymerase Promoter Template (50 ng/µl);
Klenow Enzyme (1-7.5 U/µl); and
Nuclease-Free Water.

The components were placed in numbered vials and placed in a container with a printed instruction manual for the production of amplified sRNA molecules using the kit components.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method for producing a sense RNA molecule, comprising:
   a) providing a single stranded cDNA molecule having 5' and 3' ends;
   b) attaching a homopolymeric tail for annealing a single stranded promoter template to the 3' end of said single stranded cDNA molecule using terminal deoxynucleotidyl transferase;
   c) annealing a single stranded promoter template consisting essentially of a single RNA polymerase promoter sequence at a 5' end and a sequence complementary to the homopolymeric tail at a 3' end thereof to said homopolymeric tail through base pairing with the complementary sequence of the single stranded promoter template, wherein said single stranded promoter template is not extendable with DNA polymerase;
   d) extending said homopolymeric tail such that said single stranded promoter template is converted to a double stranded promoter; and
   e) initiating RNA transcription using an RNA polymerase which recognizes said double stranded promoter,
   thereby producing a sense RNA (sRNA) molecule.

2. The method of claim 1, wherein a) comprises providing a mRNA transcript having 5' and 3' ends; and synthesizing a single stranded cDNA molecule from said mRNA transcript.

3. The method of claim 2, wherein synthesis of the single stranded cDNA molecule comprises reacting the mRNA molecule with a RNase H⁻ reverse trancriptase.

4. The method of claim 3, wherein synthesis of the single stranded cDNA molecule further comprises reacting the mRNA molecule with an oligodT primer.

5. The method of claim 3, wherein synthesis of the single stranded cDNA molecule further comprises reacting the mRNA molecule with a random-primer.

6. The method of claim 2, further comprising purifying the single stranded cDNA molecule prior to attaching the homopolymeric tail.

7. The method of claim 6, further comprising degrading the mRNA transcript prior to purifying the single stranded cDNA molecule.

8. The method of claim 2, wherein the mRNA-transcript is of mammalian origin.

9. The method of claim 2, wherein the mRNA transcript is of human origin.

10. The method of claim 2, wherein the mRNA transcript is isolated from a biological source comprising degraded RNA.

11. The method of claim 1, wherein the homopolymeric tail is a polydT tail.

12. The method of claim 1, wherein the single stranded promoter template comprises a T7, T3 or SP6 RNA Polymerase promoter.

13. The method of claim 1, wherein the single stranded promoter template is blocked at the 3' end by a 3' amino modifier, a 3' deoxyterminator, or a 3' dideoxyterminator.

14. The method of claim 1, further comprising synthesizing second strand cDNA using a random primer, thus producing random-primed second strand cDNA fragments prior to initiating RNA transcription.

15. The method of claim 14, wherein the random-primed second strand cDNA fragments are ligated together prior to initiating RNA transcription.

16. The method of claim 1, wherein RNA transcription is initiated using a T7, T3 or SP6 RNA polymerase.

17. The method of claim 1, further comprising amplifying the resulting sRNA molecule.

18. The method of claim 17, wherein sRNA amplification is initiated using a combination of oligodT and random primers.

19. The method of claim 17, wherein sRNA amplification is initiated using oligodT primers, and the resulting sRNA molecule comprises a polyA tail.

20. The method of claim 17, wherein the sRNA amplification is initiated using random primers.

21. The method of claim 1, further comprising adding a polyA tail to the resulting sRNA molecule.

22. The method of claim 21, wherein the polyA tail is added using polyA polymerase.

23. The method of claim 1, further comprising reverse transcribing the resulting sRNA molecule, thereby producing a single stranded cDNA molecule.

24. The method of claim 23, wherein the reverse transcription comprises incorporating detectably labeled nucleotides into the single stranded cDNA molecule.

25. The method of claim 24, wherein the detectably labeled nucleotides comprise a fluorescent dye.

26. The method of claim 25, wherein the fluorescent dye is cy3 or cy5.

27. The method of claim 23, further comprising attaching at least one detectable label to the resulting cDNA molecule.

28. The method of claim 27, wherein the detectable label is attached to the cDNA molecule via a nucleic acid dendrimer.

29. The method of claim 1, wherein a) comprises providing a mRNA molecule having 5' and 3' ends; and synthesizing a single stranded cDNA molecule from said mRNA molecule.

30. The method of claim 29, wherein a) further comprises adding a polyA tail to the cDNA molecule.

31. The method of claim 30, wherein the polyA tail is added using polyA polymerase.

32. The method of claim 31, wherein synthesis of the single stranded cDNA molecule further comprises reacting the mRNA molecule with an oligodT primer.

* * * * *